United States Patent [19]

Nelson et al.

[11] Patent Number: 4,536,503
[45] Date of Patent: Aug. 20, 1985

[54] NAPHTHOXYALKYLAMINES AND RELATED COMPOUNDS AS ANTIINFLAMMATORY AGENTS

[75] Inventors: Peter H. Nelson, Los Altos; Howard J. Ringold, Woodside; Stefan H. Unger; Thomas R. Thieme, both of Palo Alto, all of Calif.

[73] Assignee: Syntex (U.S.A.) Inc., Palo Alto, Calif.

[21] Appl. No.: 569,011

[22] Filed: Jan. 9, 1984

Related U.S. Application Data

[62] Division of Ser. No. 330,114, Dec. 14, 1981, abandoned.

[51] Int. Cl.³ ............... A61K 31/40; A61K 31/445; A61K 31/495
[52] U.S. Cl. .................... 514/255; 514/319; 514/428; 514/651
[58] Field of Search ............ 424/250, 330, 325, 274, 424/267

[56] References Cited

U.S. PATENT DOCUMENTS 2,133,779 10/1938 Clifford ........................ 524/246
3,810,897 5/1974 Philippe et al. ............... 424/250
3,816,430 6/1974 Santilli et al. ................. 424/330

FOREIGN PATENT DOCUMENTS 6710300 1/1968 Netherlands .

OTHER PUBLICATIONS

Derwent abstract of Japanese Pat. No. J52/083533, (7-12-77).
Derwent abstract of Japanese Pat. No. J52/023055, (2-21-77).
Uchida et al., Chem. Abstracts vol. 93:132286c (1980).

Primary Examiner—Donald G. Daus
Assistant Examiner—William A. Teoli, Jr.
Attorney, Agent, or Firm—Ellen J. Buckles; Tom M. Moran; Alan M. Krubiner

[57] ABSTRACT

Compounds of the formula:

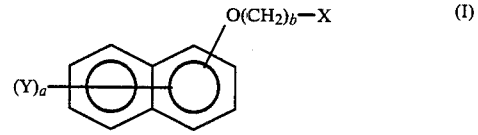

and the pharmaceutically acceptable acid addition salts thereof, wherein;
Y is halo, alkoxy, alkyl, or dialkylamino;
a is 0, 1 or 2;
b is an integer from 2–12 with the proviso that if b is 2 or 3 a cannot be 0; and
X is selected from the group consisting of: —OH, OR$^1$, —NH$_2$, —NHR$^1$, NR$_2^1$,

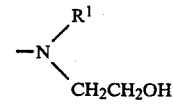

and —NHCONHR$^2$ in which
each R$^1$ is independently alkyl or cycloalkyl or in —NR$_2^1$, both R$^1$ together are alkylene or form a piperazine ring optionally substituted at the ring N by alkyl or —CH$_2$CH$_2$OH; and
R$^2$ is alkyl, cycloalkyl, or optionally substituted phenyl;
have antiinflammatory properties and are useful in the treatment of conditions characterized by inflammation and swelling.

2 Claims, No Drawings

NAPHTHOXYALKYLAMINES AND RELATED COMPOUNDS AS ANTIINFLAMMATORY AGENTS

This is a division of application Ser. No. 330,114 filed Dec. 14, 1981, now abandoned.

BACKGROUND OF THE INVENTION

This invention concerns antiinflammatory agents which are naphthyl alkyl ethers.

Antiinflammatory activity has been demonstrated for compounds representing a number of structural classes, for example, the corticosteroids, aspirin and related compounds, derivatives of arylacetic and arylpropionic acids and relatives of phenylbutazone. However, no representative of any of these classes is regarded as ideal.

Other compounds which are superficially structurally similar to the compounds of the invention are also known. Those which are closest structurally to the compounds of the present invention are among those disclosed in U.S. Pat. No. 2,133,779 which broadly discloses primary amino alkoxy-aryl compounds, as agents in preserving rubber. Exemplified in that patent as representative, is 2-aminoethyloxynaphthalene. Other naphthyl ethers which contain primary amino groups, are disclosed in Japanese Pat. Nos. J52/023055 and J52/083533 which compounds are useful in treating depression, in view of their ability to inhibit monoamine oxidase. Less similar are those compounds in Netherlands Pat. No. 67/10300 which discloses naphthyl ethers, linked through an alkylene group to a substituted phenyl, as fungicides. There are a large number of disclosures of compounds which are adrenergic blocking agents characterized by the very general structure:

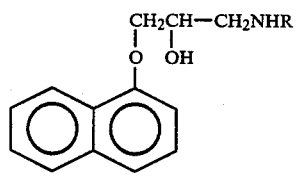

Also, short chain alkyl analogs of some of the compounds herein have been disclosed: 2-aminoethoxy naphthalenes in *J. Am. Chem. Soc.*, 72: 3846 (1950) and *Chem. Abst.* 80: 47634b; ibid, 80: 36897p, and 3-aminopropoxynaphthalene in *Chem. Abst.*, 72: 66685v.

SUMMARY OF THE INVENTION

The invention herein, in one aspect, concerns novel compounds of the formula.

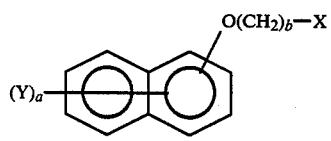

and the pharmaceutically acceptable acid addition salts thereof wherein;

Y is halo, alkoxy, alkyl, or dialkylamino;
a is 0, 1 or 2;
b is an integer from 2–12 with the proviso that if b is 2 or 3, a cannot be 0; and
X is selected from the group consisting of: —OH, $OR^1$, —$NH_2$, —$NHR^1$, $NR_2^1$,

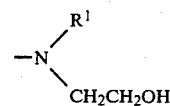

and —$NHCONHR^2$ in which
each $R^1$ is independently alkyl or cycloalkyl
or in —$NR_2^1$, both $R^1$ together are alkylene or form a piperazine ring optionally substituted at the ring N by alkyl or —$CH_2CH_2OH$; and
$R^2$ is alkyl, cycloalkyl, or optionally substituted phenyl.

In another two aspects, the invention relates to pharmaceutical compositions containing a compound of Formula I and to methods of preventing, reducing, or inhibiting inflammation utilizing compounds of formula I or the aforesaid composition. Finally, the invention also relates to a process for the preparation of compounds of formula I, and their salts.

DETAILED DESCRIPTION OF THE INVENTION

Definitions

As used herein:

"Alkyl" means a branched or unbranched saturated hydrocarbon chain containing 1–8 carbon atoms, such as methyl, ethyl, propyl, tert-butyl, n-hexyl, n-heptyl or iso-octyl and the like.

"Alkoxy" means the group —OR wherein R is alkyl as herein defined.

"Cycloalkyl" means saturated carbocyclic rings containing 5–7 carbon atoms.

"Alkylene" means $(CH_2)_n$ wherein n is an integer from 1–8.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and phenyl wherein there is substitution; "optionally followed by converting the free base to the acid addition salt" means that said conversion may or may not be carried out in order for the process described to fall within the invention, and the invention includes those processes wherein the free base is converted to the acid addition salt and those processes in which it is not.

"Optionally substituted phenyl" means a phenyl moiety, which may or may not be substituted as indicated in the previous paragraph, with 1-3 substituents selected from the group consisting of halo, lower alkyl (1-4C), lower alkoxy (1-4C), hydroxy, and trifluoromethyl.

Certain embodiments of the invention herein contain an amino nitrogen—i.e., those cases wherein X and/or Y is chosen so that a primary, secondary, or tertiary amine is in the compound. In these cases, pharmaceutically acceptable acid addition salts may be prepared.

"Pharmaceutically acceptable acid addition salt" refers to those salts which retain the biological effectiveness and properties of the free bases and which are not biologically or otherwise undesirable, formed with inorganic acids such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, menthanesulfonic acid, ethanesulfonic acid, p-toluenesulfonic acid, salicylic acid and the like.

The compounds of the invention herein will be named as naphthyloxyalkanes. The numbering system for the naphthalene nucleus in this nomenclature is shown below:

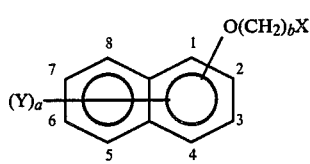

METHODS OF PREPARATION

The compounds of the invention are prepared from the corresponding substituted 1- or 2-naphthols of the formula:

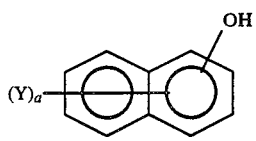

Compounds of formula A are commercially available or may easily be prepared by means well known to those in the art. The compounds of formula A are then converted to the corresponding chloroalkyl ethers by treating with the appropriate chloroalkyl tosylate as shown below:

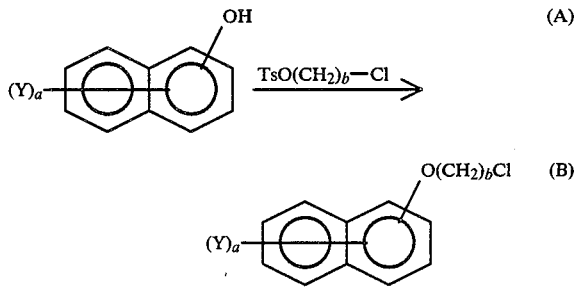

wherein the abbreviation TsO signifies the toluenesulfonyloxy group.

In carrying out this conversion, the compound of formula A is dissolved along with an approximately equi-molar amount of the appropriate chloroalkyl tosylate, and a sufficient amount of a strong base to neutralize the resulting toluenesulfonyl acid, in an inert aprotic organic solvent. The base may be, for example, potassium or sodium carbonate or potassium or sodium hydroxide, preferably potassium carbonate. The organic solvent may be, for example, dimethylformamide, tetrahydrofuran, or acetone, preferably dimethylformamide. The mixture is stirred at a temperature between about 20° C. to 90° C., preferably 55° C. to 65° C. for 1 to 40 hours, preferably about 4 hours. The product, of formula B, is then isolated by conventional means.

In carrying out the above indicated reaction and those set forth below isolation and purification of the compounds and intermediates described herein can be effected, if desired, by any suitable separation or purification procedure such as, for example, filtration, extraction, crystallization, column chromatography, thin-layer chromatography or thick-layer chromatography, or a combination of these procedures. Specific illustrations of suitable separation and isolation procedures can be had by reference to the examples hereinbelow. However, other equivalent separation or isolation procedures could, of course, also be used.

The salt products are also isolated by conventional means. For example, the reaction mixtures may be evaporated to dryness, and the salts can be further purified by conventional methods.

The compounds of formula B are then converted to the desired compounds of formula I by treatment with the appropriate reagents:

Treating with a superoxide produces compounds of Formula I wherein X is equal to —OH:

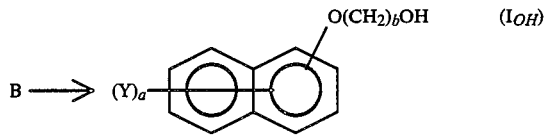

In this step, the compound of formula B is treated with a suitable superoxide, such as potassium superoxide in the presence of a complexing agent such as 1,4,7,10,13,16-hexaoxacyclooctadecane (18-Crown 6), and of an aprotic organic solvent, such as, dimethylsulfoxide. The reaction takes place at between about 10° C. and 90° C., preferably in the room temperature range, over a period of 1 to 20 hours, preferably around 10 hours.

Alternatively, the compounds of Formula I wherein X is equal to OH may be prepared directly from the corresponding naphthols by treating with an appropriate haloalkanol in the presence of base. To carry out this reaction, a mixture of the appropriate naphthol, the appropriate -haloalkanol, in approximately equi-molar quantities are mixed with a strong base, such as potassium or sodium carbonate or hydroxide, in the presence of an aprotic organic solvent such as, for example, dimethylformamide. The reaction takes considerable time, from one to ten days, usually about 6 to 8 days, when run at elevated temperatures from about 40° to 100° preferably 60° to 65°. In both of the above cases the product of Formula $I_{OH}$ is isolated conventionally.

Treating with the sodium alkoxide or cycloalkoxide results in compounds of formula I wherein X is $OR^1$:

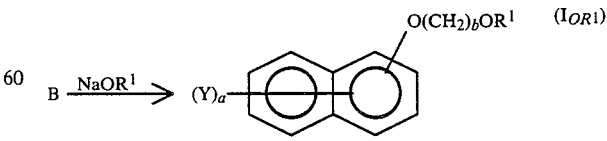

In the above conversion, a solution of the compound of formula B with the appropriate alkali metal alkoxide in approximately equi-molar amount made up in a solvent consisting of the alkanol from which the alkali metal alkoxide is derived i.e., for example, sodium methoxide in methanol, or sodium ethoxide in ethanol, preferably sodium methoxide in methanol, The solution is refluxed for 4 to 24 hours, preferably around 8 hours, and the product, of Formula $I_{OR1}$ is isolated conventionally.

Treating with the appropriately substituted amine results in compounds of formula I wherein the alkyl side chain contains a primary, secondary or tertiary amine:

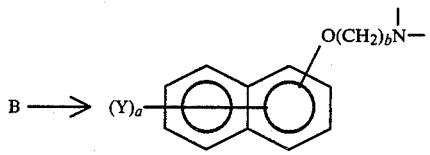

Appropriate reagents for the above conversion include potassium phthalimide, followed by hydrolysis to give the primary amine; primary or secondary amines to give secondary and tertiary amines, respectively, or a compound of the formula $R^1HNCH_2CH_2OH$.

If the product is a primary amine, the compound of formula B is preferably treated with an equi-molar amount of potassium phthalimide both reactants being dissolved in an aprotic organic solvent such as, dimethylformamide or tetrahydrofuran as indicated hereinabove. The solution is then heated at high temperature of about 100 −160° C., preferably about 140° for several hours preferably 2 to 3 hours. The resulting compound, which is the phthalimide of the compound of formula B is then isolated, if desired, and dissolved in a polar organic solvent, such as methanol or ethanol, preferably ethanol, and hydrazine hydrate is added to effect hydrolysis. The reaction mixture is heated to reflux temperature for 10 to 20 hours, preferably around 18 hours. The resulting compound of Formula I, wherein X is $NH_2$ is then isolated by conventional means.

If the compound of Formula I is a secondary or tertiary amine, the compound of formula B is refluxed with the appropriate primary or secondary amine in about 20 to 30 fold excess of the amine, optionally in the presence of a cosolvent such as, e.g., methanol, ethanol or ethylene glycol. The refluxing is carried out until the reaction is complete, usually around 30 minutes to 4 hours. The resulting compound is then isolated conventionally.

A similar procedure applies for preparation of the compounds of Formula I wherein X is $-NR^1CH_2CH_2OH$, except that the reagent is the appropriate N-alkylethanolamine.

Compounds of formula I wherein X is $-NHCONHR^2$ are prepared from the corresponding primary amines by treating with the appropriate isocyanate, of the formula $R^2NCO$.

The compound of formula I wherein X is $NH_2$ is dissolved in an inert, aprotic, organic solvent, preferably tetrahydrofuran. To the solution is then added the appropriate isocyanate of the formula $R^2NCO$, in approximately equi-molar amount. The solution is kept at approximately room temperature, and after reaction is complete the product urea is isolated conventionally.

Certain compounds of Formula I form acid addition salts, i.e., those wherein X is a primary secondary or tertiary amine, or wherein X is an N-alkylethanolamine, or wherein Y is dialkylamino. In these compounds, the compounds of formula I in free base form may be converted to the acid addition salts by treating with a stoichiometric excess of the appropriate organic or inorganic acid, such as, for example, phosphoric, pyruvic, hydrochloric or sulfuric acid and the like. Typically, the free base is dissolved in a polar organic solvent such as ethanol or methanol, and the acid added thereto. The temperature is maintained between about 0° C. and 50° C. The resulting acid addition salt precipitates spontaneously or may be brought out of solution with a less polar solvent.

The acid addition salts of the compounds of formula I may be decomposed to the corresponding free base by treating with a stoichiometric excess of a suitable base, such as potassium carbonate or sodium hydroxide, typically in the presence of aqueous solvent, and at a temperature of between about 0° C. and 50° C. The free base form is isolated by conventional means, such as extraction with an organic solvent.

Salts of the compounds of formula I may be interchanged by taking advantage of differential solubilities of the salts, volatilities or acidities of the acids, or by treating with an appropriately loaded ion exchange resin. For example, the interchange is effected by the reaction of a salt of the compounds of formula I with a slight stoichiometric excess of an acid of a lower pKa than the acid component of the starting salt. This conversion is carried out at a temperature between about 0° C. and the boiling point of the solvent being used as the medium for the procedure.

Utility and Administration

The compounds of formula I have been shown in standard laboratory tests to inhibit inflammation. Accordingly, the compounds of Formula I or their salts or pharmaceutical compositions containing them, may be used in inhibiting, preventing, or controlling inflammation in mammals.

Administration of the active compounds and salts described herein can be via any of the accepted modes of administration for agents which control inflammation. These methods include oral, parenteral and otherwise systemic or topical.

Depending on the intended mode of administration, the compositions used may be in the form of solid, semi-solid or liquid dosage forms, such as, for example, tablets, suppositories, pills, capsules, powders, liquids, suspensions, or the like, preferably in unit dosage forms suitable for single administration of precise dosages. The compositions will include a conventional pharmaceutical carrier or excipient and an active compound of Formula I or the pharmaceutically acceptable salts thereof and, in addition, may include other medicinal agents, pharmaceutical agents, carriers, adjuvants, etc.

For solid compositions, conventional non-toxic solid carriers include, for example, pharmaceutical grades of mannitol, lactose, starch, magnesium stearate, sodium saccharin, talcum, cellulose, glucose, sucrose, magnesium carbonate, and the like may be used. The active compound as defined above may be formulated as suppositories using, for example, polyalkylene glycols, for example, propylene glycol, as the carrier. Liquid pharmaceutically administerable compositions can, for example, be prepared by dissolving, dispersing, etc. an active compound as defined above and optional pharmaceutical adjuvants in a carrier, such as, for example, water, saline, aqueous dextrose, glycerol, ethanol, and the like, to thereby form a solution or suspension. If desired, the pharmaceutical composition to be administered may also contain minor amounts of nontoxic auxiliary substances such as wetting or emulsifying agents, pH buffering agents and the like, for example, sodium acetate, sorbitan monolaurate, triethanolamine sodium acetate, triethanolamine oleate, etc. Actual methods of preparing such dosage forms are known, or will be apparent, to those skilled in this art; for example, see *Remington's Pharmaceutical Sciences,* Mack Publishing Company, Easton, Pa., 15th Edition, 1975. The composition or formulation to be administered will, in any event, contain a quantity of the active compound(s) in an amount effective to alleviate the symptoms of the subject being treated.

For the compounds of formula I, either oral or topical administration is preferred depending on the nature of the disorder being treated.

For oral administration, a pharmaceutically acceptable non-toxic composition is formed by the incorporation of any of the normally employed excipients, such as, for example pharmaceutical grades of mannitol, lactose, starch, magnesium stearate, sodium saccharin, talcum, cellulose, glucose, sucrose, magnesium, carbonate, and the like. Such compositions take the form of solutions, suspensions, tablets, pills, capsules, powders, sustained release formulations and the like. Such compositions may contain 1%–95% active ingredient, preferably 25–70%.

For topical administration, these compositions comprise an effective amount of a compound of this class in admixture with a pharmaceutically acceptable non-toxic carrier. A suitable range of composition would be 0.1%–10% active ingredient, and the balance carrier, preferably 1–2% active ingredient. The concentration of active ingredient in pharmaceutical compositions suitable for topical application will vary depending upon the particular activity of the compound used in conjunction with the condition and subject to be treated. Suitable carriers or medicament vehicles for topical application of these compounds include creams, ointments, lotions, emulsions, solutions and the like.

For example, a suitable ointment for topical application of compounds of the instant invention contains 15 to 45 percent of a saturated fatty alcohol having 16 to 24 carbon atoms such as cetyl alcohol, stearyl alcohol, behenyl alcohol, and the like and 45 to 85 wt. percent of a glycol solvent such as propylene glycol, polyethylene glycol, dipropylene glycol, and mixtures thereof. The ointment can also contain 0 to 15 wt. percent of a plasticizer such as polyethylene glycol, 1,2,6-hexanetriol, sorbitol, glycerol, and the like; 0 to 15 wt. percent of a coupling agent such as a saturated fatty acid having from 16 to 24 carbon atoms, e.g., stearic acid, palmitic acid, behenic acid, a fatty acid amide e.g., oleamide, palmitamide, stearamide, behenamide and an ester of a fatty acid having from 16 to 24 carbon atoms such as sorbitol monostearate, polyethylene glycol monostearate, polypropylene glycol or the corresponding monoester of other fatty acids such as oleic acid and palmitic acid; and 0 to 20 wt. percent of a penetrant such as dimethyl sulfoxide, dimethylacetamide.

The amount of active compound administered will of course, be dependent on the subject being treated, the severity of the affliction, the manner of administration and the judgment of the prescribing physician. However, an effective dosage is in the range of 1–100 mg/kg/day, preferably about 25 mg/kg/day. For an average 70 kg human, this would amount to 70 mg–7 g per day, or preferably about 1.5 g/day.

Preferred Embodiments

Preferred among the compounds of the invention are those, and their pharmaceutically acceptable salts, wherein a is 0. Preferred among these, are those wherein b is an integer from 4 to 8.

Expecially preferred are those compounds, and their pharmaceutically acceptable salts, which are selected from the group consisting of:
1-(1-naphthyloxy)-8-(N,N-dimethylamino)octane;
1-(1-naphthyloxy)-8-(N-phenyl-N-(2-hydroxyethyl)amino)octane;
1-(1-naphthyloxy)-8-(N-ethyl-N-(2-hydroxyethyl)amino)octane;
2-(1-naphthyloxy)-8-(N-ethyl-N-(2-hydroxyethyl)amino)octane;
1-(1-naphthyloxy)-8-(N,N-diethylamino)octane;
1-(1-naphthyloxy)-6-aminohexane;
1-(1-naphthyloxy)-6-(N,N-dimethylamino)hexane; and
1-(1-naphthyloxy)-8-(pyrrolidin-1-yl)octane.

The following examples serve to illustrate the invention. They should not be construed as narrowing it, or limiting its scope.

PREPARATION 1

Preparation of 1-(p-Toluenesulphonyloxy)-8-chlorooctane p-Toluenesulphonyl chloride (20.5 g) was added to a mixture of 8-chloro-1-octanol (17.7 g) and pyridine (50 ml) of 0°. After a hour the solution was added to ice and the mixture was extracted with ether. The ethereal solution was washed with dilute hydrochloric acid, dried with magnesium sulfate, and evaporated to yield the title compound as an oil.

PREPARATION 2

Preparation of 1-(2-Naphthyloxy)-8-chloro-octane

A. A mixture of 2-naphthol (17.5 g), 1-(p-toluenesulphonyloxy)-8-chlorooctane (32.0 g), anhydrous potassium carbonate (32.0 g) and dimethylformamide (200 ml) was stirred at 60° for 4 hours. Water and ether were then added, and the ethereal solution was washed with water and dilute aqueous potassium hydroxide, then dried and evaporated. The residue was chromotographed on silica gel, eluting with 3:2 hexane:dichloromethane, to afford the title compound as a solid, mp 35°.

B. Similarly, using the procedure in paragraph A, but substituting 1-naphthol for 2-naphthol, the corresponding -haloalkyl 1-naphthyl ethers are prepared.

EXAMPLE 1

Preparation of 1-(2-naphthyloxy)8-(N-ethyl-N-(2-hydroxyethyl)aminooctane 1-(2-naphthyloxy)-8-chlorooctane (11.0 g) was refluxed for 40 minutes in (ethylamino)-ethanol (100 ml). The solution was poured into water and extracted with ether. The ethereal solution was extracted with dilute hydrochloric acid, and the extract then basified with aqueous potassium hydroxide. The alkaline solution was extracted with ether, and the extract was dried and evaporated to yield the title compound as an oil, which was converted to the hydrochloride, mp 73°–4°.

EXAMPLE 2

Preparation of 8-(1-naphthyloxy)-1-aminoctane

A solution of 1-(1-naphthyloxy)-8-chlorooctane (9.5 g) and potassium phthalimide (8.4 g) in dimethylformamide (50 ml) was heated at 140° for 3 hours. The solution was poured into water and extracted with dichloromethane; the extract was washed, dried and evaporated and the residue was crystallized from acetone hexane to afford the intermediate N-8-(1-naphthyloxy)octylphthalimide mp 63°–64°.

A mixture of the above prepared N-8-(1-naphthyloxy)octylphthalimide (10.0 g), ethanol (200 ml) and hydrazine hydrate (3.2 ml) was refluxed for 18 hours. The solution was evaporated to a 100 ml, and diluted with water (200 ml), then basified with aqueous potassium hydroxide and extracted with hexane. The extract was washed, dried and evaporated to give the title compound as an oil which was converted to the hydrochloride, mp 90.5°–92°.

EXAMPLE 3

Preparation of $N^1$-cyclohexyl-$N^{28}$-(1-naphthyloxy)octylurea

Cyclohexylisocyanate (0.5 ml) was added to a solution of 8-(1-naphthyloxy)-1-aminooctane (0.95 g) in tetrahydrofuran (25 ml). After 15 minutes the solution was added to water and extracted with dichloromethane. The extract was washed with dilute hydrochloric acid, dried and evaporated. The residue was crystallized from ethyl acetate-hexane to produce the title compound, mp 100°–101°.

EXAMPLE 4

Preparation of 4-(1-naphthyloxy)-1-methoxybutane

A solution of 4-(1-naphthyloxy)-butyl chloride (3.0 g) and sodium methoxide (1.5 g) in methanol (25 ml) was refluxed for 8 hours, then poured into water and the solution extracted with ether. The extract was dried and evaporated and the residue chromatographed on silica gel, eluting with 2:1 hexane ether, to produce the title compound as an oil.

EXAMPLE 5

Preparation of 4-(1-naphthyloxy)-1-butanol

Potassium superoxide (0.71 g) was added to a solution of 4-(1-naphthyloxy)butyl chloride (2.0 g) and 18-Crown-6 (0.5 g) in dimethylsulfoxide (10 ml). After 8 hors the mixture was added to water and the solution was extracted with ether. The ethereal solution was dried and evaporated and the residue chromatographed on silica gel, eluting with 2:1 hexane ether, to yield the title compound as an oil.

EXAMPLE 6

Preparation of 8-(2-naphthyloxy)-1-octanol

A mixture of 2-naphthol (28.8 g), 8-chloro-1-octanol (32.8 g), potassium carbonate (40 g) and dimethylformamide (200 ml) was stirred at 60°–65° for 7 days. Water and ether were then added. The a solution was washed with aqueous potassium hydroxide, dried and evaporated. The residue was chromatographed on silica gel, eluting with 95:5 dichloromethane:methanol, and the product so obtained was crystallized from hexane, to give the title compound, mp 67°–9°.

EXAMPLE 7

A. Similarly, using the procedure outlined in Examples 1–5, the following compounds of the invention were prepared as their salts and may, if desired, be converted by the method of Example 9 to the free base form:

In the table below, Y, X, a, and b are as herein defined.

| Position of ether | Y | a | b | X | Form | m.p. |
|---|---|---|---|---|---|---|
| 1 | — | 0 | 4 | $NH_2$ | maleate | 99–102[ |
| 1 | — | 0 | 4 | $NH_2$ | hydrochloride | 150–151.5[ |
| 1 | — | 0 | 4 | $N(CH_3)_2$ | maleate | 83–86[ |
| 1 | — | 0 | 4 | OH | — | oil |
| 1 | — | 0 | 5 | $NH_2$ | hemimaleate | 169–172[ |
| 1 | — | 0 | 5 | $N(CH_3)_2$ | maleate | 104–105[ |
| 1 | — | 0 | 6 | $N(CH_3)_2$ | maleate | 96–98[ |
| 1 | — | 0 | 6 | $NH_2$ | hemimaleate | 112–114[ |
| 1 | — | 0 | 8 | $N(CH_3)_2$ | maleate | 90–92[ |
|  | — | 0 | 8 | $N(CH_3)_2$ | hydrochloride | 142–143.5[ |
| 1 | — | 0 | 8 | $NHC_6H_5$ | hydrochloride | 103–105[ |
| 1 | — | 0 | 8 | $N(C_2H_5)CH_2CH_2OH$ | free base | 51–52[ |
| 1 | — | 0 | 8 | $N(C_2H_5)CH_2CH_2OH$ | hydrochloride | 118–120[ |
| 1 | — | 0 | 8 | $NHCONHC_6H_5$ | free base | 108–110[ |
| 1 | — | 0 | 8 | piperidino (N-cyclohexyl ring) | hydrochloride | 135–138[ |
| 2 | — | 0 | 8 | $N(C_2H_5)CH_2CH_2OH$ | hydrochloride | 73–74[ |
| 2 | — | 0 | 8 | $N(CH_3)_2$ | hydrochloride | 141–143[ |
| 1 | — | 0 | 8 | $NHCONHC_6H_{11}$ | free base | 100–101[ |
| 2 | — | 0 | 8 | $NH_2$ | hydrochloride | 169–170[ |
| 1 | — | 0 | 8 | $N(C_2H_5)_2$ | hydrochloride | 132–133[ |
| 1 | — | 0 | 8 | $NH_2$ | hydrochloride | 90.5–92[ |
| 1 | — | 0 | 10 | $NH_2$ | hydrochloride | 84–86[ |
| 1 | — | 0 | 10 | $N(CH_3)_2$ | hydrochloride | 116–118[ |
| 1 | — | 0 | 12 | $N(CH_3)_2$ | hydrochloride | 103–105[ |
| 1 | — | 0 | 12 | $NH_2$ | hydrochloride | 72–75[ |

B. Additionally, following the procedure set forth in Preparations 1 and 2 and of the appropriate example chosen from Examples 1–5; the following are prepared:

1-(6,7-dichloronaphthyl-1-oxy)-7-heptanol;
1-(5,8-diethoxynaphthyl-2-oxy)-9-(di-n-butylamino)nonane;
11-(6,7-di-n-propylnaphthyl-1-oxy)-11-(ethoxy)undecane;
$N^1$-(6-(5,8-dimethoxynaphthyl-2-oxy)hexyl)-$N^2$-cyclohexyl urea;
1-(6-methoxynaphthyl-1-oxy)-8-(N,N-dimethylamino)octane;
1-(6-methoxynaphthyl-1oxy)-6-(N,N-dimethylamino)hexane;
1-(6-dimethylaminonaphthyl-2-oxy)-10-(4-methylpiperazin-1-yl)decane;
1-(6,7-dibromonaphthyl-2-oxy)-7-(N-phenyl-N-(2-hydroxyethyl)amino)heptane; and
1-(5,8-diethylnaphthyl-2-oxy)-12-(N-n-butylamino)dodecane.

EXAMPLE 8

Conversion of Free Base to Salt

A twofold stoichiometric excess of 3% hydrogen chloride in methanol is added to a solution of 1.0 g. of 1-(1-naphthyloxy)-8-(N,N-dimethylamino)octane in 20 ml methanol. Diethyl ether is added until precipitation is complete. The product is filtered, washed with ether, air dried and recrystallized to give 1-(1-naphthyloxy)-8-(N,N-dimethylamino)octane hydrochloride, m.p. 142°–143.5° C.

In a similar manner, all compounds of Formula I in free base form may be converted to the acid addition salts by treatment with the appropriate acid, for example, hydrochloric acid, hydrobromic acid, sulfuric acid, nitric acid, phosphoric acid, acetic acid, propionic acid, glycolic acid, pyruvic acid, oxalic acid, malonic acid, succinic acid, malic acid, maleic acid, fumaric acid, tartaric acid, citric acid, benzoic acid, cinnamic acid, mandelic acid, methanesulfonic acid, ethanesulfonic acid, p-toluenesulfonic acid, and the like.

EXAMPLE 9

Conversion of Salt to Free Base 1.0 g of 1-(1-naphthyloxy)-8-(N,N-dimethylamino)octane.HCl suspended in 50 ml of ether is stirred with a twofold stoichiometric excess of dilute aqueous potassium carbonate solution until the salt is completely dissolved. The organic layer is then separated, washed twice with water, dried over magnesium sulfate and evaporated to yield 1-(1-naphthyloxy)-8-(N,N-dimethylamino)octane as the free base.

EXAMPLE 10

Direct interchange of acid addition salts 1-(1-naphthyloxy)-8-(N,N-dimethylamino)octane acetate (1.0 g) is dissolved in 50 ml water containing a stoichiometric equivalent of sulfuric acid, and the solution evaporated to dryness. The product is suspended in ethanol and filtered, air dried and recrystallized from methanol/acetone to yield 1-(1-naphthyloxy)-8-(N,N-dimethylamino)octane bisulfate.

In Examples 10 through 15, the active ingredient is 1-(1-naphthyloxy)-8-(N,N-dimethylamino)octane; however other compounds of Formula I and the pharmaceutically acceptable salts thereof may be substituted therein.

EXAMPLE 11

| Ingredients | Quantity per tablet, mgs. |
| --- | --- |
| Active ingredient | 25 |
| cornstarch | 20 |
| lactose, spray-dried | 153 |
| magnesium stearate | 2 |

The above ingredients are thoroughly mixed and pressed into single scored tablets.

EXAMPLE 12

| Ingredients | Quantity per tablet, mgs. |
| --- | --- |
| Active ingredient | 100 |
| lactose, spray-dried | 148 |
| magnesium stearate | 2 |

The above ingredients are mixed and introduced into a hard-shell gelatin capsule.

EXAMPLE 13

| Ingredients | Quantity per tablet, mgs. |
| --- | --- |
| Active ingredient | 108 |
| lactose | 15 |
| cornstarch | 25 |
| magnesium stearate | 2 |

The above ingredients are mixed and introduced into a hard-shell gelatin capsule.

EXAMPLE 14

| Ingredients | Quantity per tablet, mgs. |
| --- | --- |
| Active ingredient | 150 |
| lactose | 92 |

The above ingredients are mixed and introduced into a hard-shell gelatin capsule.

EXAMPLE 15

An injectable preparation buffered to a pH of 7 is prepared having the following composition:

| Ingredients | |
| --- | --- |
| Active ingredient | 0.1 g |
| fumaric acid | 0.5 g |
| sodium chloride | 2.0 g |
| methyl paraben | 0.1 g |
| granulated sugar | 25.5 g |
| sorbitol (70% solution) | 12.85 g |
| Veegum K (Vanderbilt Co.) | 1.0 g |
| distilled water q.s. to | 100 ml |

EXAMPLE 16

A topical formulation is prepared as follows.
The composition contains:

|  | % wt./wt. |
| --- | --- |
| Active ingredient | 0.5 |
| Methyl paraben | 0.025 |
| Propyl paraben | 0.015 |
| Sodium lauryl sulfate | 1.0 |
| Propylene glycol | 12.0 |
| Stearyl alcohol | 25.0 |
| White petrolatum | 25.0 |
| Purified water qs. ad. | 100.0 |

The stearyl alcohol and white petrolatum are heated on a steam bath to about 75°. The other ingredients, previously dissolved in the water and warmed to 75°, are added with stirring. Stirring is continued until the mixture congeals.

What is claimed:

1. A method for inhibiting, preventing, or reducing inflammation, which method comprises administering to a subject in need of such treatment a therapeutically effective amount of a compound of the formula:

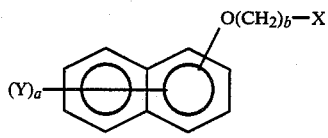

wherein;

Y is halo, alkoxy containing 1–8 carbon atoms, alkyl containing 1–8 carbon atoms, or dialkylamino in which each alkyl group contains 1–8 carbon atoms;

a is 0, 1 or 2;

b is an integer from 2–12 with the proviso that if b is 2 or 3 a cannot be 0; and X is selected from the group consisting of: $-NH_2$, $-NHR^1$, $NR_2^1$, and

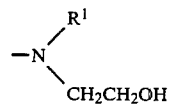

in which each $R^1$ is independently alkyl containing 1–8 carbon atoms, cycloalkyl containing 5–7 carbon atoms, or in $-NR_2^1$, both $R^1$ together form a or pyrrolidine, piperidine or piperazine ring, said piperazine ring being optionally substituted at the ring N by alkyl containing 1–8 carbon atoms, or $-CH_2CH_2OH$ or a pharmaceutically acceptable acid addition salt thereof.

2. A method for inhibiting, preventing, or reducing inflammation, which method comprises administering to a subject in need of such treatment a therapeutically effective amount of a compound selected from the group consisting of;

1-(1-naphthyloxy)-8-(N,N-dimethylamino)octane;
1-(1-naphthyloxy)-8-(N-phenyl-N-(2-hydroxyethyl-)amino)octane;
1-(1-naphthyloxy)-8-(N-ethyl-N-(2-hydroxyethyl)-amino)octane;
1-(2-naphthyloxy)-8-(N-ethyl-N-(2-hydroxyethyl)-amino)octane;
1-(1-naphthyloxy)-8-(N,N-diethylamino)octane;
1-(1-naphthyloxy)-6-aminohexane;
1-(1-naphthyloxy)-6-(N,N-dimethylamino)hexane; and
1-(1-naphthyloxy)-8-(pyrrolidin-1-yl)octane.

* * * * *